US008092999B2

(12) United States Patent
Takagi

(10) Patent No.: US 8,092,999 B2
(45) Date of Patent: Jan. 10, 2012

(54) BIOLOGICAL SAMPLE REACTION CHIP AND BIOLOGICAL SAMPLE REACTION METHOD

(75) Inventor: Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 361 days.

(21) Appl. No.: 12/360,136

(22) Filed: Jan. 27, 2009

(65) Prior Publication Data

US 2009/0197274 A1 Aug. 6, 2009

(30) Foreign Application Priority Data

Feb. 1, 2008 (JP) ................................ 2008-022675

(51) Int. Cl.
*C12Q 1/68* (2006.01)
*C12P 19/34* (2006.01)

(52) U.S. Cl. ........................ 435/6.1; 435/6.11; 435/6.12

(58) Field of Classification Search ........................ None
See application file for complete search history.

(56) References Cited

U.S. PATENT DOCUMENTS 6,124,138 A * 9/2000 Woudenberg et al. ........ 436/518
6,436,722 B1 8/2002 Clark et al.
7,261,859 B2 * 8/2007 Andersson et al. ............. 422/72
7,465,562 B2 12/2008 Wangh et al.
2003/0040021 A1 2/2003 Clark et al.
2007/0099290 A1 * 5/2007 Iida et al. ................... 435/287.2
2009/0111170 A1 4/2009 Wangh et al.

FOREIGN PATENT DOCUMENTS

| | | |
|---|---|---|
| JP | 2000-236876 | 9/2000 |
| JP | 2003-532118 | 10/2003 |
| JP | 2006-126010 | 5/2006 |
| JP | 2006-126011 | 5/2006 |
| JP | 2006-528002 | 12/2006 |
| JP | 2007-322204 | 12/2007 |
| JP | 2008-122151 | 5/2008 |
| JP | 2008-122152 | 5/2008 |
| WO | WO2005/024436 | 3/2005 |

* cited by examiner

*Primary Examiner* — Young J Kim
(74) *Attorney, Agent, or Firm* — Harness, Dickey & Pierce, P.L.C.

(57) ABSTRACT

A biological sample reaction chip, including: a plurality of reaction containers; a reaction liquid introduction channel having a reaction liquid supply opening at a first end and an evacuation opening at a second end; and a reaction liquid quantifying channel, a third end of which is connected to one of the reaction containers, and a fourth end of which is connected to the reaction liquid introduction channel, wherein an interior of each of the reaction containers is coated with a reagent that is necessary for a reaction.

3 Claims, 5 Drawing Sheets

10

BIOLOGICAL SAMPLE REACTION CHIP AND BIOLOGICAL SAMPLE REACTION METHOD

CROSS-REFERENCES TO RELATED APPLICATIONS

This application relates to and claims priority from Japanese Patent Application No. 2008-022675, filed on Feb. 1, 2008, the entire disclosure of which is incorporated herein by reference.

BACKGROUND

1. Technical Field

The present invention relates to a biological sample reaction chip and to a biological sample reaction method for carrying out biological sample reactions such as nucleic acid amplification.

2. Related Art

Growing attention is being focused on methods for carrying out, for instance, chemical analysis, chemical synthesis or bio-related analysis using microfluidic chips in which micro-channels are provided in a glass plate or the like. Microfluidic chips, which are also called micro-Total Analytical Systems (micro-TAS), Lab-on-a-chip and the like, are advantageous in that they require smaller amounts of specimens and reagents, have shorter reaction times and generate fewer waste products than existing devices. Thus, microfluidic chips are thus a promising application in a wide range of fields such as medical diagnosis, environmental and foodstuff onsite analysis, and in the manufacture of pharmaceuticals and chemicals, where test costs can be reduced since reaction amounts may be small. Likewise, testing can be made more efficient by considerably shortening also reaction times, since samples and reagents are used in small amounts. When used in medical diagnosis, in particular, microfluidic chips are advantageous in that they can use less of a specimen, for instance a blood sample, which allows easing the burden placed on the patient.

Known methods for amplifying genes such as DNA and RNA, used as samples, include polymerase chain reaction (PCR). In PCR, a mixture of target DNA and reagents is placed in a tube where the reagents and the target DNA are made to react, by repeating a so-called thermal cycle that involves changes of temperature in three stages, for instance, 55° C., 72° C. and 94° C., over several minutes, using a temperature control device. In each temperature cycle the target DNA can be amplified, to roughly a double amount, through the action of an enzyme called polymerase.

So-called real-time PCR, using special fluorescent probes, has come into use in recent years. In real-time PCR, DNA can be quantified while the amplification reaction is taking place. Real-time PCR boasts high measurement sensitivity and reliability, and is hence widely used in research and clinical testing.

Conventional devices, however, were problematic in that the amount of reaction liquid required for PCR is normally of several tens of μl, while basically only one gene could be determined in one reaction system. Some methods allow measuring simultaneously about four genes by introducing plural fluorescent probes and discriminating between respective colors, but determining simultaneously more than four genes inevitably calls for an increase in the number of reaction systems. The amount of DNA extracted from the specimen is normally small, and reagents are expensive. It has been thus difficult to determine simultaneously multiple reaction systems.

JP-A-2006-126010 and JP-A-2006-126011 disclose inventions in which liquid analyte samples such as a PCR reaction solution or blood are accurately introduced into a plurality of chambers, using a rotationally driven device.

JP-A-2000-236876 discloses a method that involves preparing micro-wells integrated on a semiconductor substrate, and carrying out PCR in the wells, to amplify and analyze collectively multiple DNA samples, using small sample amounts.

SUMMARY

An advantage of some aspects of the invention is to provide a biological sample reaction chip and a biological sample reaction method that allow a reaction to be carried out with a small amount of reaction liquid and that allow processing efficiently multiple specimens at a time.

A biological sample reaction chip according to an aspect of the invention includes: a plurality of reaction containers; a reaction liquid introduction channel having a reaction liquid supply opening at a first end and an evacuation opening at a second end; and a reaction liquid quantifying channel, a third end of which is connected to one of the reaction containers, and a fourth end of which is connected to the reaction liquid introduction channel, such that an interior of each of the reaction containers is coated with a reagent that is necessary for a reaction.

In this case, a reaction liquid is fed from the reaction liquid introduction channel into the reaction containers via the reaction liquid quantifying channels. Reactions using extremely small amounts of reaction liquid are made possible thereby, something that is difficult to achieve by pipette quantifying. The cost of reagents and so forth can be reduced when using small amounts reaction liquid. Also, reaction times are shortened considerably, which enhances processes efficiency. Moreover, reactions can take place in multiple reaction containers at a time, which allows conducting multiple tests and the like with good efficiency.

The reaction liquid is introduced into the reaction containers after having resided in the reaction liquid quantifying channels, whereby contamination between reaction containers can be prevented.

Reagents necessary for the reactions are coated on each reaction container, and hence the user can easily conduct tests and the like simply by filling reaction liquid.

A volume of the reaction containers may be smaller than A volume of the reaction liquid quantifying channels.

A biological sample reaction method according to an aspect of the invention is a biological sample reaction method using the above-mentioned biological sample reaction chip, the method including: reducing the pressure inside the reaction containers, the reaction liquid quantifying channels and the reaction liquid introduction channel to a predetermined pressure; filling a reaction liquid into the reaction liquid introduction channel via the reaction liquid supply opening; introducing the reaction liquid into the reaction liquid quantifying channels by reverting the pressure inside the reaction containers, the reaction liquid quantifying channels and the reaction liquid introduction channel to a pressure outside the chip; removing the reaction liquid from the reaction liquid introduction channel; introducing into the reaction containers the reaction liquid in the reaction liquid quantifying channels, by centrifugal force; and carrying out a biological sample reaction process.

In this case, a reaction liquid is fed from the reaction liquid introduction channel into the reaction containers via the reaction liquid quantifying channels. Reactions using extremely small amounts of reaction liquid are made possible thereby, something that is difficult to achieve by pipette quantifying. The cost of reagents and so forth can be reduced when using small amounts reaction liquid. Also, reaction times are shortened considerably, which enhances processes efficiency. Moreover, reactions can take place in multiple reaction containers at a time, which allows conducting multiple tests and the like with good efficiency.

The reaction liquid is introduced into the reaction containers after having resided in the reaction liquid quantifying channels, whereby contamination between reaction containers can be prevented.

In the reduction of the pressure to the predetermined pressure, the pressure is preferably reduced to a pressure ranging from 50% of the pressure outside the chip to less than the pressure outside the chip.

That way, the reaction liquid is prevented from reaching the reaction containers during introduction of the reaction liquid into the reaction liquid quantifying channels. Also prevented is contamination across neighboring reaction containers, via the reaction liquid quantifying channels and the reaction liquid introduction channel, which occurs when certain reagents applied beforehand on the reaction containers leach out into the reaction liquid.

The biological sample reaction process may be a process including nucleic acid amplification, the reaction liquid may have a target nucleic acid, an enzyme for amplifying nucleic acid and nucleotides, at predetermined concentrations, and the reaction containers may be coated beforehand with primers.

When carrying out real-time PCR, fluorescent probes may be applied beforehand in the reaction apparatus.

DESCRIPTION OF EXEMPLARY EMBODIMENTS

An embodiment of an aspect of the invention is explained below with reference to accompanying drawings.

Embodiment 1

Figure 1A:
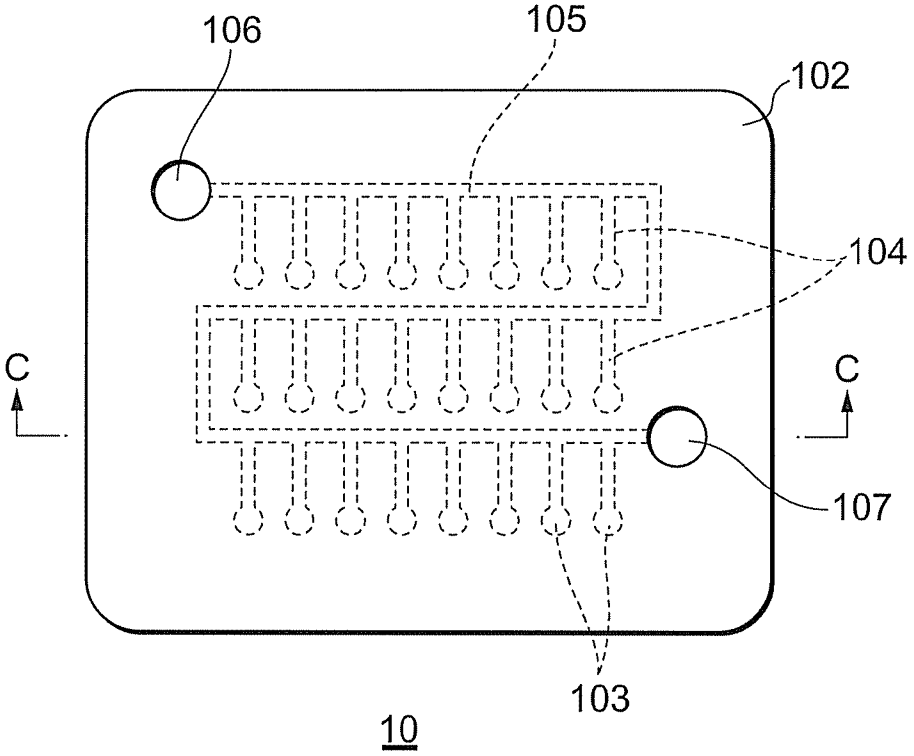
FIG. 1A is a top-side view diagram illustrating the schematic constitution of a microreactor array according to Embodiment 1 of an aspect of the invention.
Figure 1B:
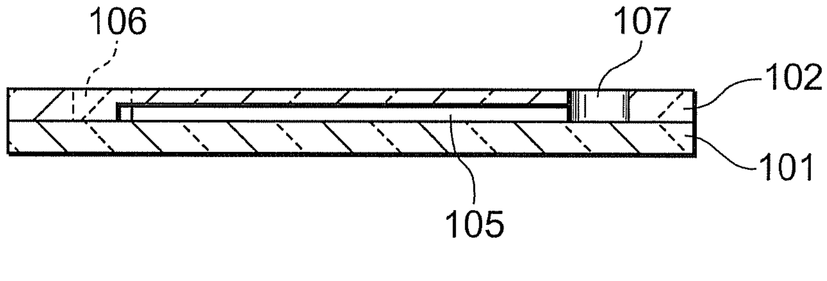
FIG. 1B is a cross-sectional diagram of FIG. 1A along line C-C.

FIG. 1A is a top-side view diagram illustrating the schematic constitution of a microreactor array (biological sample reaction chips) 10 according to Embodiment 1 of an aspect of the invention, and FIG. 1B is a cross-sectional diagram of FIG. 1A along line C-C. As illustrated in the figure, the microreactor array 10 has a transparent plate (first plate) 101, a transparent plate (second plate) 102, reaction container 103, reaction liquid quantifying channels 104, a reaction liquid introduction channel 105, a reaction liquid supply opening 106, and an evacuation opening 107.

As illustrated in FIG. 1, the microreactor array 10 is configured by the transparent plate 101 and the transparent plate 102 bonded together. The transparent plate 101 has formed therein the reaction container 103, the reaction liquid quantifying channels 104 and the reaction liquid introduction channel 105. The transparent plate 102 has formed therein the reaction liquid supply opening 106 and the evacuation opening 107. The transparent plates 101, 102 may be, for instance, resin plates.

The reaction container 103 are formed, for instance, to a circular shape having a diameter of 500 μm and a depth of 100 μm. The reaction liquid quantifying channels 104 and the reaction liquid introduction channel 105 are formed so that the cross section thereof perpendicular to the direction of reaction liquid flow is 100 μm wide and 100 μm deep. The reaction liquid quantifying channels 104 are formed to a length of 3 mm along the direction of reaction liquid flow. The volume of the reaction container 103 is smaller than the volume of the reaction liquid quantifying channels 104. Preferably, the reaction container 103, the reaction liquid quantifying channels 104 and the reaction liquid introduction channel 105 are subjected to a treatment that renders the inner wall surfaces thereof hydrophilic, in order to prevent bubble adhesion. Preferably, the inner wall surfaces of the reaction container 103, the reaction liquid quantifying channels 104 and the reaction liquid introduction channel 105 are subjected to a surface treatment that inhibits nonspecific adsorption of biomolecules such as proteins. Also, the surfaces of the transparent plate 101 and the transparent plate 102 that come into contact with each other are preferably subjected to a surface treatment for imparting liquid repellency, with a view to preventing contamination across neighboring reaction container 103 during preliminary application of primers and fluorescent probes, necessary for PCR reactions, on the reaction container 103.

A method of filling reaction liquid into the microreactor array 10 is explained next.

Figure 2:
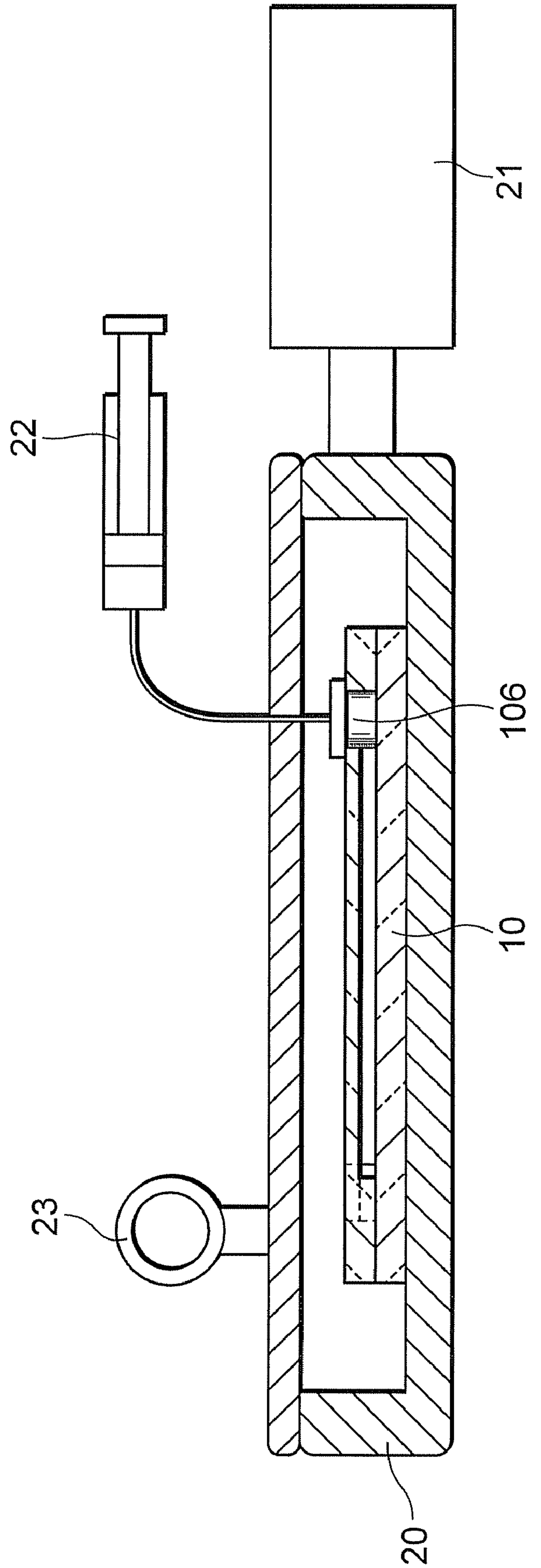
FIG. 2 is a schematic diagram illustrating an example of a device for reducing pressure inside the microreactor array.

Firstly, as illustrated in FIG. 2, the microreactor array 10 is placed in an airtight container 20 provided with a pressure gauge 23, and then the pressure is reduced to 60 kPa by way of a vacuum pump 21. Thereby, the pressure inside the microreactor array 10 (inside the reaction container 103, the reaction liquid quantifying channels 104 and the reaction liquid introduction channel 105) is brought down to 60 kPa. A syringe pump 22 for reaction liquid filling is connected to the reaction liquid supply opening 106 of the microreactor array 10. With the pressure in the airtight container 20 kept at 60 kPa, the reaction liquid is fed into the reaction liquid introduction channel 105 using the syringe pump 22.

The reaction liquid includes a target nucleic acid, a polymerase and nucleotides (dNTPs) at predetermined concentrations suitable for reaction.

As the target nucleic acid there may be used, for instance, DNA extracted from biological samples such as blood, urine, saliva or spinal fluid, or cDNA reverse-transcribed from extracted RNA.

The primers may be present in the reaction liquid, although in the microreactor array of the present example the primers are applied beforehand on the reaction container 103, where they are held in a dry state. Different primers may be applied on respective reaction container 103, so that multiple PCR reactions can be carried out simultaneously.

Figure 3:
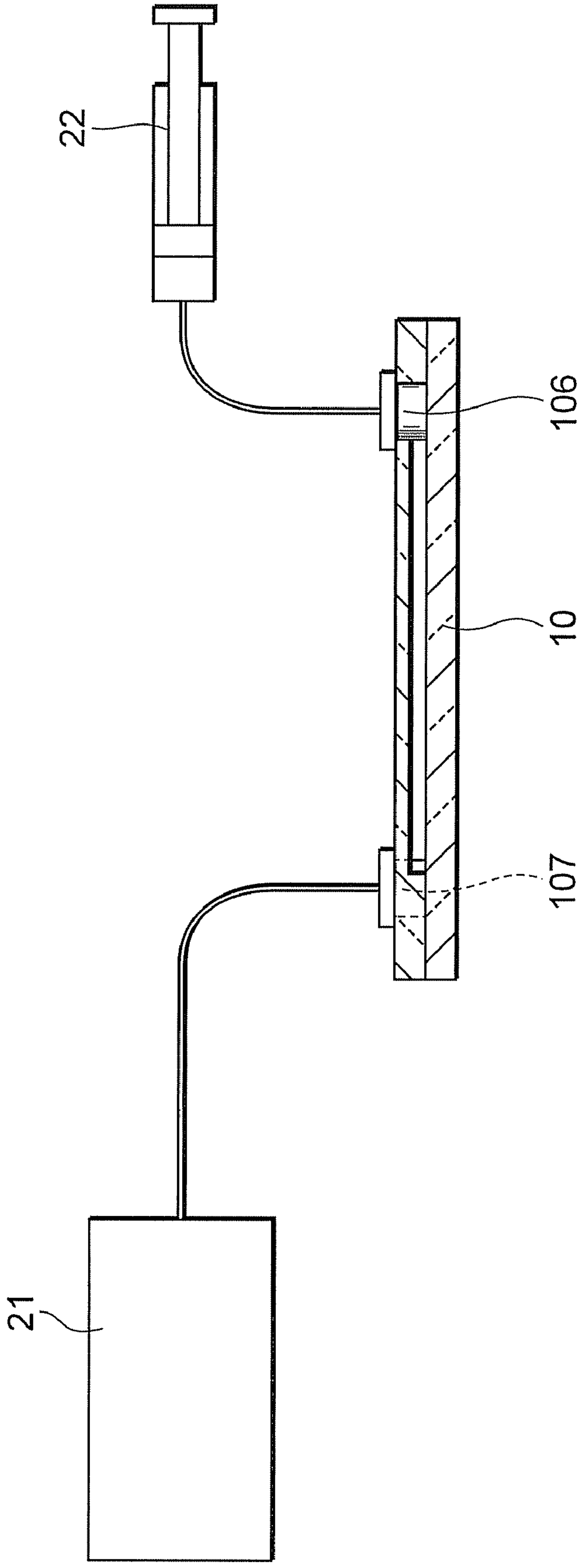
FIG. 3 is a schematic diagram illustrating another method of reducing pressure inside the microreactor array.

Reduction of pressure in the microreactor array 10 may also be accomplished by directly connecting the vacuum pump 21 to the evacuation opening 107, as illustrated in FIG. 3, without resorting to an airtight container 20 such as the one illustrated in FIG. 2.

Figure 4B:
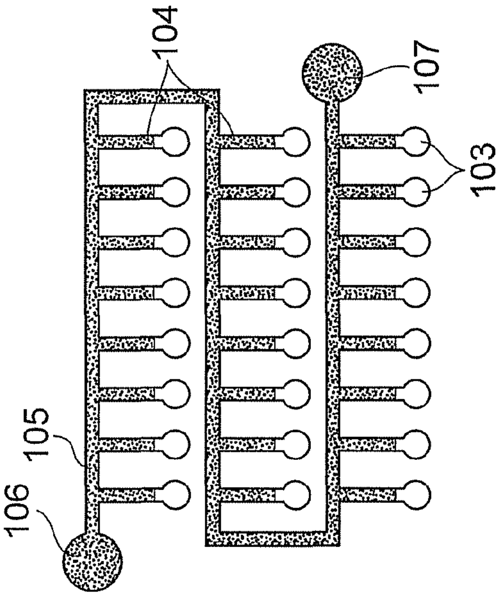
FIG. 4A, FIG. 4B, FIG. 4C, and FIG. 4D are schematic diagrams for explaining a method of filling a reaction liquid into the microreactor array.
Figure 4D:
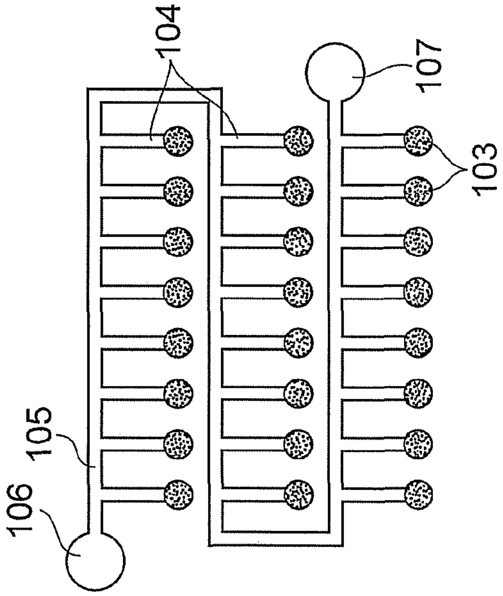
Figure 4A:
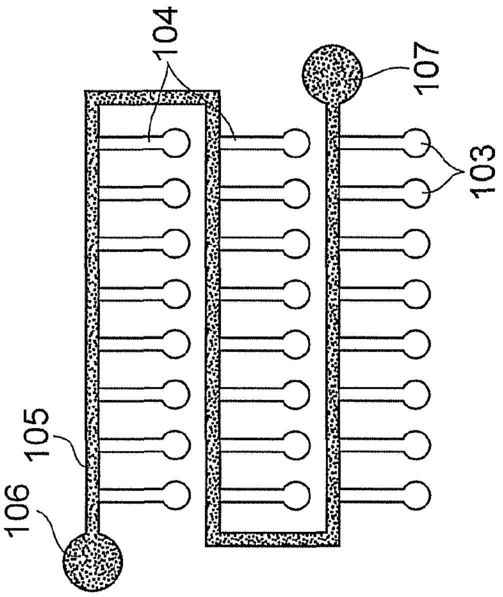

Next, the pressure inside the microreactor array 10 is brought back to atmospheric pressure. At the stage in which reaction liquid is fed into the reaction liquid introduction channel 105, the reaction liquid lingers in the reaction liquid introduction channel 105 without flowing into the reaction liquid quantifying channels 104, as illustrated in FIG. 4A. The purpose of this is to balance capillary forces and atmospheric pressure in the reaction liquid quantifying channels 104 and the reaction container 103 connected thereto. When the pressure inside the microreactor array 10 is reverted to atmospheric pressure, a given amount V of reaction liquid flows from the reaction liquid introduction channel 105 into the reaction liquid quantifying channels 104, as illustrated in FIG. 4B. The liquid amount V is the amount of reaction liquid that ultimately fills the reaction container 103.

Herein, the relationship of equation (1) below holds-initially:

$$V/(V1+V2)=(P0-Pc)/P0 \quad (1)$$

wherein Pc denotes the set pressure (in this case 60 kPa) when the interior of the microreactor array 10 is evacuated, V1 denotes the volume of the reaction container 103, V2 denotes the volume of the reaction liquid quantifying channels 104, P0 denotes the atmospheric pressure (≈100 kPa) and V denotes the amount of reaction liquid introduction from the reaction liquid quantifying channels 104 into the reaction container 103.

The liquid amount V can thus be obtained from equation (2) below.

$$V=(V1+V2)\times(P0-Pc)/P0 \quad (2)$$

Assuming P0=100 kPa, and since Pc=60 kPa, reaction liquid flows into each reaction liquid quantifying channel 104 in an amount of equivalent to 40% of the aggregate volume (V1+V2) of the reaction container 103 and the reaction liquid quantifying channels 104.

Preferably, the set pressure Pc ranges from 50% of the atmospheric pressure P0 to less than the atmospheric pressure P0.

By setting thus the pressure Pc to range from 50% of the atmospheric pressure P0 to less than the atmospheric pressure P0, the amount of liquid introduced from the reaction liquid introduction channel 105 into the reaction liquid quantifying channels 104 is no greater than 50% of the aggregate volume (V1+V2) of the reaction container 103 and the reaction liquid quantifying channels 104. Setting V1<V2, as described above, and keeping the amount of liquid flowing into the reaction liquid quantifying channels 104 within the above range has the effect of preventing the reaction liquid from reaching the reaction container 103. If the reaction liquid flows into the reaction container 103, the reagent applied beforehand in the reaction container 103 may leach out into the reaction liquid, which may result in contamination across neighboring reaction container 103 via the reaction liquid quantifying channels 104 and the reaction liquid introduction channel 105.

Figure 4C:
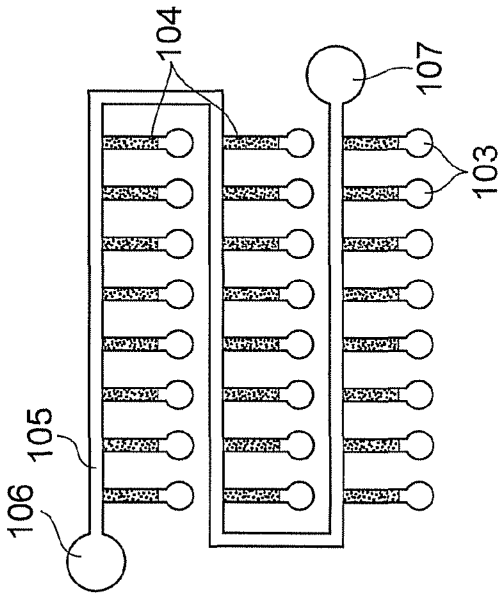

Next, the reaction liquid remaining in the reaction liquid introduction channel 105 is suctioned off and removed using a syringe or the like, as illustrated in FIG. 4C. Subsequently, the reaction liquid supply opening 106 and the evacuation opening 107 are sealed with adhesive sheet or the like, and the microreactor array 10 is rotated using a centrifugation device 30 such as the one illustrated in FIG. 5.

Figure 5:
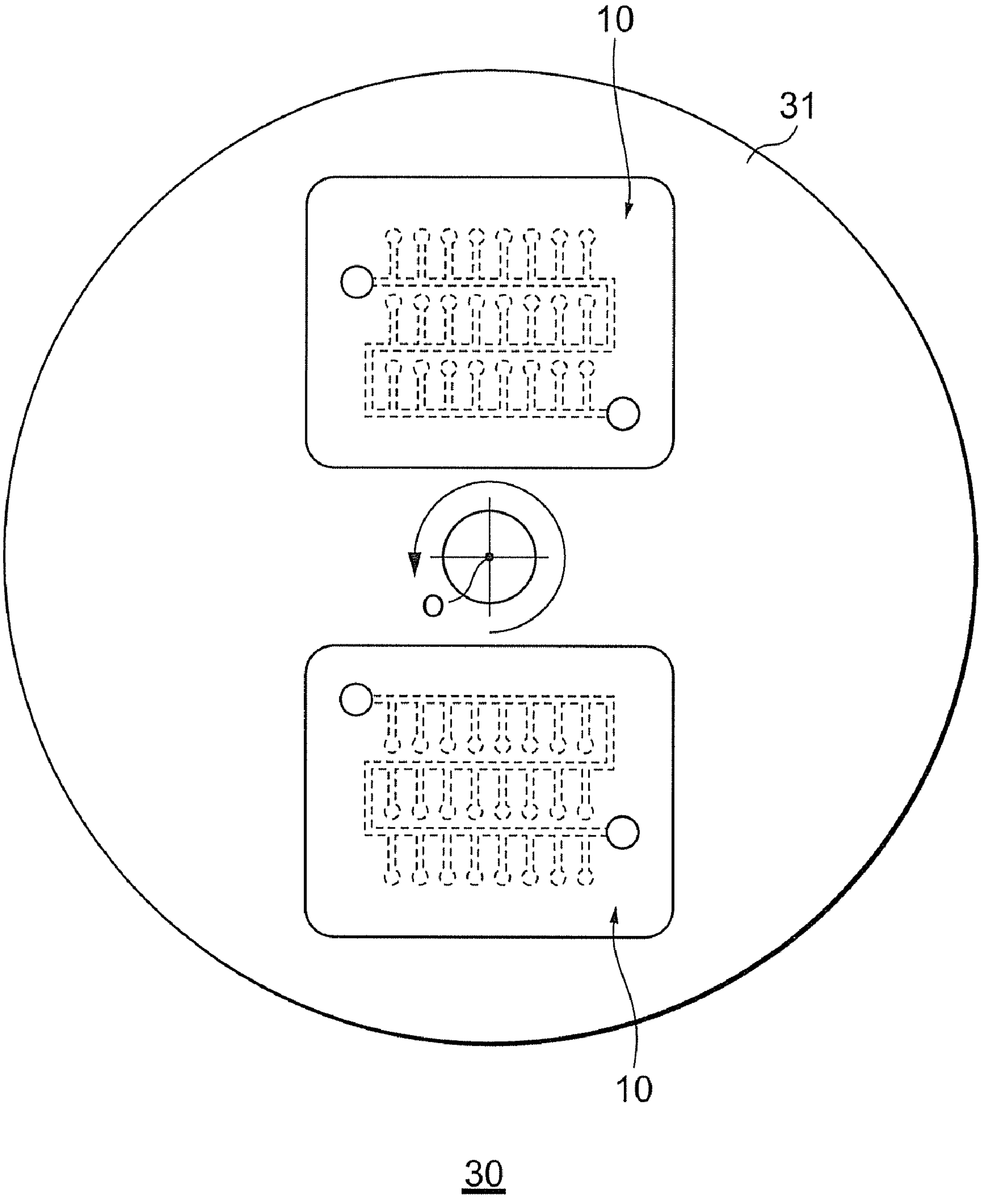
FIG. 5 is a diagram illustrating the schematic constitution of a centrifugation device that imparts centrifugal force on the microreactor array.

The microreactor array 10 is placed on a rotary table 31 of the centrifugation device 30, as illustrated in FIG. 5. Rotation of the centrifugation device 30 causes then centrifugal force to act in the microreactor array 10, in the direction running from the reaction liquid quantifying channels 104 towards the reaction container 103.

The reaction liquid in the reaction liquid quantifying channels 104 moves into the reaction container 103 as a result of the centrifugal force acting on the microreactor array 10. The specific gravity of the air in the reaction container 103 is smaller than that of the reaction liquid, and hence the air in the reaction container 103 is pushed out into the reaction liquid introduction channel 105 via the reaction liquid quantifying channels 104. Air is thus replaced with the reaction liquid, which fills as a result the reaction container 103.

PCR (biological sample reaction treatment) is carried out then, once the reaction liquid is fed into the microreactor array 10 in accordance with the above procedure. To carry out the PCR process, the transparent plate 102 is fixed at a predetermined position and the microreactor array 10 is placed in a thermal cycler. PCR involves ordinarily repeating cycles that has each a step of denaturating double-stranded DNA at 94° C., a subsequent step of annealing with primers at about 55° C., and a step of replicating complementary strands, at about 72° C., using a thermostable DNA polymerase.

When real-time PCR is to be carried out in the microreactor array 10, the inner walls of the reaction container 103 are coated beforehand with fluorescent probes and the primers used in the PCR reaction, with fluorescence intensity being measured at each cycle using a CCD sensor or the like. The amount of initial target nucleic acid is calculated and measured on the basis of the cycle at which a specific fluorescence intensity is reached. The method for carrying out real-time PCR is not limited to the above one. For instance, fluorescent probes may be rendered unnecessary when using a double-strand binding fluorescent dye such as SYBR(™) Green.

In Embodiment 1, thus, centrifugal force is used to feed reaction liquid into the reaction container 103 via the reaction liquid quantifying channels 104. Reactions using extremely small amounts of reaction liquid are made possible thereby, something that is difficult to achieve by pipette quantifying. Moreover, the reactions can take place in multiple reaction container 103 at a time, which allows conducting multiple tests with good efficiency.

The reaction liquid is introduced into the reaction container 103 after having resided in the reaction liquid quantifying channels 104, whereby contamination across reaction container 103 can be prevented.

In Embodiment 1, the microreactor array 10 is used in a reaction apparatus for real-time PCR, but may also be used for various reactions that utilize genetic or biological samples. For instance, the microreactor array 10 may be used in a process for detecting target proteins in a reaction liquid, by coating the reaction container 103 with, for instance, peptides (oligonucleotides) or proteins such as antigens, antibodies, receptors or enzymes that selectively capture (adsorb or bind to) specific proteins.

What is claimed is:

1. A biological sample reaction method using a biological sample reaction chip, the biological sample reaction chip including:

a plurality of reaction containers;

a reaction liquid introduction channel having a reaction liquid supply opening at a first end and an evacuation opening at a second end; and a plurality of reaction liquid quantifying channels communicating with the reaction containers, respectively, each of the reaction liquid quantifying channels having a third end connected to one of the reaction containers, a fourth end connected to the reaction liquid introduction channel, and a volume which is bigger than a volume of the reaction container, an interior of each of the reaction containers being coated with a reagent that is necessary for a reaction, the biological sample reaction method comprising:

reducing the pressure inside the reaction containers, the reaction liquid quantifying channels and the reaction liquid introduction channel to a predetermined pressure;

filling a reaction liquid into the reaction liquid introduction channel via the reaction liquid supply opening;

introducing the reaction liquid into the reaction liquid quantifying channels by reverting the pressure inside the reaction containers, the reaction liquid quantifying channels and the reaction liquid introduction channel to a pressure outside the chip;

removing the reaction liquid from the reaction liquid introduction channel;

introducing into the reaction containers the reaction liquid in the reaction liquid quantifying channels, by centrifugal force; and carrying out a biological sample reaction process, wherein in said filling the reaction liquid into the reaction liquid introduction channel, the reaction liquid lingers in the reaction liquid introduction channel without flowing into the reaction liquid quantifying channels, in said introducing the reaction liquid into the reaction liquid quantifying channels, the reaction liquid is prevented from reaching the reaction containers.

2. The biological sample reaction method according to claim 1, wherein in the reduction of the pressure to the predetermined pressure, the pressure is reduced to a pressure ranging from 50% of the pressure outside the chip to less than the pressure outside the chip.

3. The biological sample reaction method according to claim 1, wherein the biological sample reaction process is a process including nucleic acid amplification, the reaction liquid has a target nucleic acid, an enzyme for amplifying nucleic acid and nucleotides, at predetermined concentrations, and the reaction containers are coated beforehand with primers.

* * * * *